(12) United States Patent
Hudson (10) Patent No.: US 8,356,527 B2
(45) Date of Patent: Jan. 22, 2013

(54) INSPECTION APPARATUS HAVING AN INSERTION TUBE WITH DISPERSED HEALING AGENT

(75) Inventor: Craig Alan Hudson, Skaneateles, NY (US)

(73) Assignee: GE Inspection Technologies, LP, Lewistown, PA (US)

( * ) Notice: Subject to any disclaimer, the term of this patent is extended or adjusted under 35 U.S.C. 154(b) by 1203 days.

(21) Appl. No.: 12/187,418

(22) Filed: Aug. 7, 2008

(65) Prior Publication Data

US 2010/0036321 A1    Feb. 11, 2010

(51) Int. Cl.
*G01N 19/00* (2006.01)
(52) U.S. Cl. ........................ 73/865.8; 604/140
(58) Field of Classification Search .................. None
See application file for complete search history.

(56) References Cited

U.S. PATENT DOCUMENTS

2005/0281520 A1* 12/2005 Kehoskie et al. ............. 385/117

OTHER PUBLICATIONS

S. White, N. Sottos, J. Moore. E. Brown, A. Jones, J. Rule, Autonomic Healing of Polymers and Composites. Theoretical and Applied Mechanics, University of Illinois Urbana-Champaign, Urbana, Illinois 61801, Aerospace Engineering, University of Illinois Urbana-Champaign, Urbana, Illinois 61801, Chemistry, University of Illinois Urbana-Champaign, Urbana, Illinois 61801, XXI International Congress of Theoretical and Applied Mechanics, Warsaw, Poland, Aug. 15-21, 2004 (2 pp).

Ms. Jody W.C. Pang, Dr. Ian P. Bond, A Hollow Fibre Reinforced Polymer Composite Encompassing Self-Healing and Enhanced Damage Visibility, University of Bristol, Department of Aerospace Engineering, Queen's Building, University Walk, Bristol. BS8 1TR. UK. Tel: +44 (0) 117 928 8662 Fax: +44 (0) 117 927 2771 E-mail: I.P.Bond@Bristol.ac.uk (Mar. 8, 2005) (18 pp).

M.R. Kessler, N.R. Sottos, S.R. White, Self-Healing Structural Composite Materials, Department of Mechanical Engineering, University of Tulsa, 600 South College Avenue, Tulsa, OK 74104, USA, Department of Aerospace Engineering, University of Illinois at Urbana-Champaign, Urbana, Illinois 61801, USA, Department of Theoretical and Applied Mechanics, University of Illinois at Urbana-Champaign, Urbana, Illinois 61801, USA, Beckman Institute for Advanced Science and Technology, University of Illinois at Urbana-Champaign, Urbana, Illinois 61801, USA, received Jan. 24, 2003; revised Feb. 26, 2003; accepted Mar. 18, 2003 (11 pp).

Brown, E. N., Sottos, N. R. Performance of Embedded Microspheres for Self-Healing Polymer Composites, SEM IX International Congress on Experimental Mechanics; Orlando, FL; USA; Jun. 5-8, 2000. (4 pp.).

Stauth Sean A., Parviz Babak A., Self-Assembled Single-Crystal Silicon Circuits on Plastic, Department of Electrical Engineering, The Paul G. Allen Center for Computer Science and Engineering, University of Washington, Room AE100R, Campus Box 352500, Seattle, WA 98195-2500 Published in PNAS, Sep. 19, 2006, vol. 103, No. 38 (6 pp.).

(Continued)

*Primary Examiner* — Hezron E Williams
*Assistant Examiner* — Mark A Shabman
(74) *Attorney, Agent, or Firm* — Global Patent Operation; Mark Conklin (57) ABSTRACT

An elongated insertion tube can be provided having a wall having one or multiple layers. A layer of a wall can include composite material having healing agent storage structures that store healing agent material and a catalyst dispersed within a polymer matrix. The layer can be formed so that when force is imparted to the layer, healing agent material stored within a storage structure reacts with a catalyst and polymerizes, to heal damage imparted to the layer.

10 Claims, 5 Drawing Sheets

OTHER PUBLICATIONS

Alan S. Jones, Joseph D. Rule, Jeffrey S. Moore, Scott R. White, and Nancy R. Sottos, Catalyst Morphology and Dissolution Kinetics of Self-Healing Polymers, Theoretical and Applied Mechanics Department, Department of Chemistry, and Department of Aerospace Engineering, University of Illinois, Urbana, Illinois 61801, Received Aug. 18, 2005. Revised Manuscript Received Jan. 3, 2006, Published on the Web Feb. 3, 2006 (6 pp).

Jean-Marie Lehn, Toward Complex Matter: Supramolecular Chemistry and Self-Organization, Institut de Science et d'Ingénierie Supramoléculaires, Université Louis Pasteur, 67000 Strasbourg, France and Collége de France, 75005 Paris, France. Published in PNAS, Apr. 16, 2002, vol. 99, No. 8 (6 pp.).

M. R. Kessler and S. R. White, Self-Activated Healing of Delamination Damage in Woven Composites, Department of Theoretical and Applied Mechanics, University of Illinois at Urbana-Champaign, Urbana-Champaign, IL, USA, Department of Aeronautical and Astronautical Engineering, University of Illinois at Urbana-Champaign, Urbana-Champaign, IL, USA, Accepted Aug. 30, 2000, Available online Mar. 6, 2001. Can be found in Composites: Part A 32 (2001) 683-699. URL: www.elsevier.com/locate/compositesa (17 pp).

E. N. Brown, M. R. Kessler, N. R. Sottos and S. R. White. In Situ Poly(Urea-Formaldehyde) Microencapsulation of Dicyclopentadiene, Department of Theoretical and Applied Mechanics, Department of Aeronautical & Astronautical Engineering, University of Illinois at Urbana-Champaign, Talbot Laboratory, 104 S. Wright St, Urbana, IL 61801, USA, Department of Mechanical Engineering, The University of Tulsa, Keplinger Hall, 600 South College Ave., Tulsa, OK 74104, USA (Received Feb. 15, 2003; accepted May 4, 2003) Published in Journal of Microencapsulation ISSN 0265-2048 print/ISSN 1464-5246 online at 2003 Taylor & Francis Ltd, http://www.tandf.co.uk/journals (12 pp).

E.N. Brown, S.R. White, N.R. Sottos. Retardation and Repair of Fatigue Cracks in a Microcapsule Toughened Epoxy Composite—Part II: In Situ Self-Healing. Department of Theoretical and Applied Mechanics and the Beckman Institute for Advanced Science and Technology, University of Illinois at Urbana-Champaign, Urbana, IL 61801, USA. Department of Aerospace Engineering and the Beckman Institute for Advanced Science and Technology, University of Illinois at Urbana-Champaign, Urbana, IL 61801, USA. Corresponding Author. Present address: Materials Science and Technology Division, Los Alamos National Laboratory, MS-E544, Los Alamos, NM 87545, USA. Received Jan. 26, 2005; revised Apr. 19, 2005;accepted Apr. 20, 2005. Available online Jul. 6, 2005 @2005 Elsevier Ltd. (16 pp).

Sylvain Vauthey, Steve Santoso, Haiyan Gong, Nicki Watson, and Shuguang Zhang, Molecular Self-Assembly of Surfactant-Like Peptides to Form Nanotubes and Nanovesicles. Center for Biomedical Engineering, 56-341, Massachusetts Institute of Technology, 77 Massachusetts Avenue, Cambridge, MA 02139-4307; †Department of Biology, Massachusetts Institute of Technology, Cambridge, MA 02139; §W. M. Keck Imaging Facility, Whitehead Institute, Cambridge, MA 02142; and ‡Department of Ophthalmology, Boston University School of Medicine, 715 Albany Street, Boston, MA 02118. Communicated by John M. Buchanan, Massachusetts Institute of Technology, Cambridge, MA (received for review Nov. 17, 2001). Published in PNAS, Apr. 16, 2002, vol. 99, No. 8 (6 pp.).

Soo Hyoun Cho, H. Magnus Andersson, Scott R. Mite, Nancy R. Sottos, and Paul V. Braun, Polydimethylsiloxane-Based Self-Healing Materials. Adv. Mater. 2006, 18, 997-1000 © 2006 Wiley-VCH Verlag GmbH & Co. KGaA, Weinheim. (4 pp).

J. B. Ennis, F. W. MacDougall, R.A. Cooper, J. Bates, General Atomics Energy Products, Repetitive Pulse Application of Self-Healing High Voltage Capacitors. Presented at: International Power Modulator Conference Hollywood, California Jul. 1-3, 2002 © 2002 IEEE (6 pp).

Shawn H. Phillips, Timothy S. Haddad, and Sandra J. Tomczak. Developments in Nanoscience: Polyhedral Oligomeric Silsesquioxane (POSS)-Polymers. Air Force Research Laboratory, Edwards AFB, CA 93524-7680, USA. ERC Inc., Edwards AFB, CA 93524-7680, USA. Received Mar. 4, 2004; accepted Mar. 4, 2004. Available online Apr. 12, 2004. (37 pp).

Kyle A. Williams, Andrew J. Boydston and Christopher W. Bielawski. Towards Electrically Conductive, Self-Healing Materials. Department of Chemistry and Biochemistry, The University of Texas at Austin, 1 University Station A5300, Austin, TX 78712, USA. Received Sep. 27, 2006. Accepted Nov. 28, 2006. This journal is @2007 The Royal Society. J. R. Soc. Interface (2007) 4, 359-362. doi:10.1098/rsif.2006.0202. Published online Jan. 3, 2007. (4 pp).

Thomas Clifford, Ahmad Abushamleh, and Daryle H. Busch. Factors Affecting the Threading of Axle Molecules Through Macrocycles: Binding Constants for Semirotaxane Formation. Department of Chemistry, Malott Hall, University of Kansas, Lawrence, KS 66045; and Department of Chemistry, Hashemite University, Zarqa 13115, Jordan. Edited by Jack Halpern, University of Chicago, Chicago, IL, and approved Jan. 24, 2002 (received for review Dec. 2, 2001) Published in PNAS, Apr. 16, 2002, vol. 99, No. 8 (7 pp.).

R.S. Trask, H. R. Williams and I. P. Bond. Self-Healing Polymer Composites: Mimicking Nature to Enhance Performance. Department of Aerospace Engineering, University of Bristol, Queen's Building, University Walk, Bristol, BS8 1TR, UK. Print publication: Issue 1 (Mar. 2007). Bioinspiration and Biomimetics, 2 P1-P9 Received Sep. 14, 2006, accepted for publication Dec. 1, 2006. Published Jan. 12, 2007. (12 pp).

Thomas A. Plaisted, Alireza Vakil Amirkhizi, Diego Arbelaez, Syrus C. Nemat-Nasser, and Sia Nemat-Nasser. Self-Healing Structural Composites With Electromagnetic Functionality. Smart Structures and Materials 2003. vol. SPIE-5054, pp. 372-381. 2003 (10 pp).

Jean-Marie Lehn, Supramolecular Chemistry; From Molecular Information Towards Self-Organization and Complex Matter. Science vol. 295, Mar. 29, 2002. (4 pp).

Jong Keun Lee, Sun Ji Hong, and Xing Liu, Characterization of Dicyclopentadiene and 5-Ethylidene-2-Norbornene as Self-Healing Agents for Polymer Composite and Its Microcapsules Department of Polymer Science and Engineering, Kumoh National Institute of Technology, Gumi, Gyungbuk 730-701, Korea. Sung Ho Yoon School of Mechanical Engineering, Kumoh National Institute of Technology, Gumi, Gyungbuk 730-701, Korea. Received May 27, 2004; Revised Sep. 3, 2004 Macromolecular Research, vol. 12, No. 5, pp. 478-483 (2004) (6 pp).

Christopher Bergendorff, Self Healing Plastic. URL: http://www.sciencentral.com/articles/view.php3?type=article&article_id=218392982 (First published 2007) (2 pp).

Kristin Leutwyler. Self-Healing Plastics, Scientific American, Feb. 15, 2001 (1 p).

Caruso, M.M., Delafuente, D.A., Ho, V., Moore, J.S., Sottos, N.R., and White, S.R., Solvent-Promoted Self-Healing Materials, Macromolecules 40, 8830-8832 (2007). (3 pp).

Potisek, S., Davis, D.A., Sottos, N.R., White, S.R. and Moore, J.S., Mechanophore-Linked Addition Polymers, JACS129, 13808-13809 (2007). (2 pp).

Keller, M.K., White, S.R., and Sottos, N.R., A Self-Healing Poly(Dimethyl Siloxane) Elastomer, Adv. Func. Materials,17, 2399-2404 (2007). (6 pp).

Toohey, K.S., Sottos, N.R., Lewis, J.A., Moore, J.S., and White, S.R., Self-Healing Materials With Microvascular Networks, Nature Materials, 6, 581-585 (2007). (5 pp).

Rule, J.D., Sottos, N.R., White, S.R. Effect of Microcapsule Size on the Performance of Self-Healing Polymers, Polymer, 48, 3520-3529 (2007). (10 pp).

A.S. Jones, J.D. Rule, J.S. Moore, N.R. Sottos, S.R. White, "Life extension of self-healing polymers with rapidly growing fatigue cracks", J. Royal Society: Interface, 4(13), 2007, pp. 395-403. (9 pp).

Sottos, N., White, S., and Bond, I. Introduction: Self-Healing Polymers and Composites, Special Issue. J. Royal Society: Interface 4 347-348 (2007). (2 pp).

T.C. Mauldin, J.D. Rule, N.R. Sottos, S.R. White, J.S. Moore, "Self-healing kinetics and the stereoisomers of dicyclopentadiene", J. Royal Society: Interface, 4(13), 2007, pp. 389-393. (5 pp).

O'Brien, D.J., Sottos, N.R. and White, S.W., Cure-Dependent Viscoelastic Poisson's Ratio of Epoxy, Experimental Mechanics,47, 237-249 (2007). (13 pp).

J.D. Rule, E.N. Brown, N.R. Sottos, S.R. White, J.S. Moore, "Wax-protected catalyst microspheres for efficient self-healing materials", Advanced Materials, 17(2), 2005, pp. 205-208. (4 pp).

D. Therriault, S.R. White, J.A. Lewis, "Chaotic mixing in three-dimensional microvascular networks fabricated by direct-write assembly", Nature Materials, 2(4), 2003, pp. 265-271. (7 pp).

M.R. Kessler, S.R. White, "Cure kinetics of the ring-opening metathesis polymerization of dicydopentadiene" Journal of Polymer Science: Part A. Polymer Chemistry, 40(14), 2002, pp. 2373-2383. (11 pp).

J.D. Rule, J.S. Moore, "ROMP Reactivity of endo- and exo-Dicyclopentadiene", Macromolecules, 35(21), 2002, pp. 7878-7882. (5 pp).

R. Wool, "A material fix", Nature, 2001 409, 794-797. (2 pp).

S.R. White, N.R. Sottos, J. Moore, P. Geubelie, M. Kessler, E. Brown, S. Suresh, S. Viswanathan. "Autonomic healing of polymer composites", Nature, 409, 2001, pp. 794-797. (4 pp).

* cited by examiner

INSPECTION APPARATUS HAVING AN INSERTION TUBE WITH DISPERSED HEALING AGENT

BACKGROUND OF THE INVENTION

The invention relates to inspections in general and in particular to inspection apparatuses having insertion tubes for carrying out inspections.

Inspection apparatuses such as visual inspection apparatuses, eddy current sensing apparatuses, and ultrasonic sensing apparatuses are subject to being damaged or degraded during use. Many such apparatuses include elongated probes, otherwise known as insertion tubes for fitting into remote areas, such as remote areas of equipment articles, naturally occurring geographic formations and other cavernous bodies. Such insertion tubes become contacted with the walls of the bodies they are inserted into when they are inserted and removed from such bodies. When contacted, the insertion tubes are subject to damage from externally located bodies.

In many instances, insertion tubes have an internally disposed rigid structure. For example in one embodiment, an elongated helical shaped "monocoil" metal member can be disposed within an elongated insertion probe for providing crush resistance thereto. Other insertion tubes can include rigid metallic structures for providing manually controlled bending of an insertion tube. Some insertion tubes are known to include bending necks whose bending can be controlled by manual input control of an operator. Insertion tube bending necks can comprise a series of disks (washers) disposed such that bending can be controlled by the spacing and the angle between various ones of the disks.

Insertion tubes are subject to being damaged not only by forces imparted by exterior located bodies but also by forces imparted by rigid interior structure of an insertion tube, such as crush resistance providing structures and structures for allowing bending of an insertion tube.

If an insertion tube wall becomes punctured, a number of problems can occur. Notably, moist air or particulate can invade an insertion tube and propagate through a device including control circuitry and other component. Shortings of electrical circuit components have been observed.

BRIEF DESCRIPTION OF THE INVENTION

In one embodiment of the invention, an elongated insertion tube can be provided having a wall having one or multiple layers. A layer of a wall can include composite material having healing agent storage structures that store healing agent material and a catalyst dispersed within a polymer matrix. The layer can be formed so that when force is imparted to the layer, healing agent material stored within a storage structure reacts with a catalyst and polymerizes, to heal damage imparted to the layer.

BRIEF DESCRIPTION OF THE DRAWINGS

The features described herein can be better understood with reference to the drawings described below. The drawings are not necessarily to scale, emphasis instead generally being placed upon illustrating the principles of the invention. In the drawings, like numerals are used to indicate like parts throughout the various views.

DETAILED DESCRIPTION OF THE INVENTION

Figure 1:
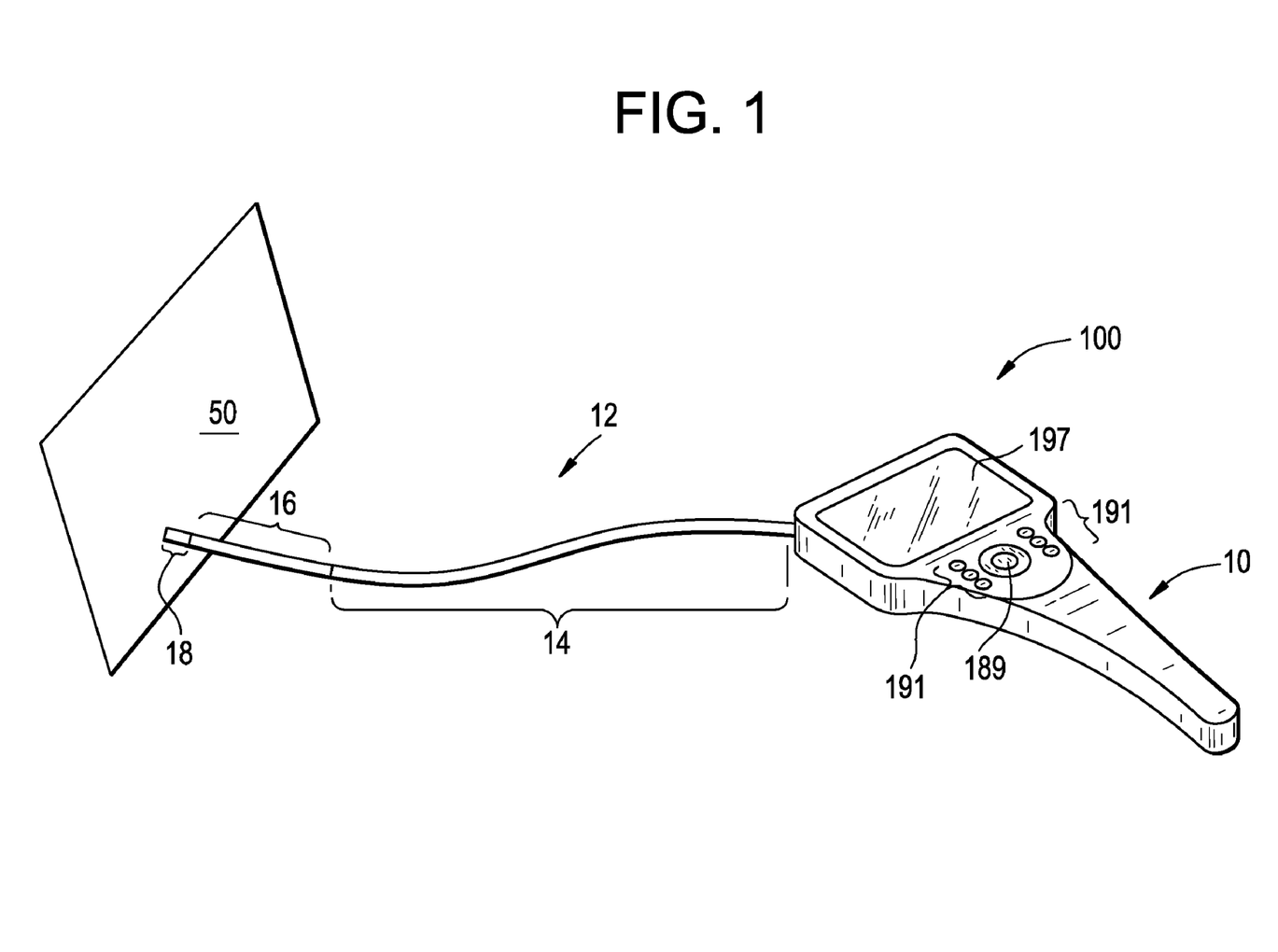
FIG. 1 is a physical form view of an insertion tube being used to inspect an article.

An exemplary inspection apparatus 100 is shown in FIG. 1. Inspection apparatus 100 can include a control and display module 10 and an insertion tube 12 extending from the control and display module 10. Inspection apparatus 100 in the embodiment shown is provided by a visual inspection apparatus for inspecting equipment articles. In another embodiment, an insertion tube equipped apparatus can be provided by an eddy current sensing apparatus. In another embodiment, an insertion tube equipped apparatus can be provided by an ultrasonic sensing apparatus.

Insertion tube 12 in the exemplary embodiment of FIG. 1 can include a main body section 14, a bending neck 16, and a camera head assembly 18, including an image sensor. Insertion tube 12 entirely or partially through its length can be of multilayer stacked up construction. At least one layer of insertion tube 12 can be formed from a composite including a plurality of particularly formed healing agent storage structures and a catalyst dispersed in a polymer matrix. The catalyst, in one embodiment, can be in the form of a plurality of particles (comprising, e.g., individual molecules or clusters of molecules), with the plurality of particles being dispersed in the polymer matrix. The insertion tube 12 can be constructed so that when force is imparted to an insertion tube, healing agent material stored in a healing agent storage structure is released to react with the catalyst to cause polymerization and healing of damage caused by the imparted force. The at least one layer formed as described can be regarded as a self healing layer and can be disposed in a particular location or locations of an insertion tube.

Figure 2:
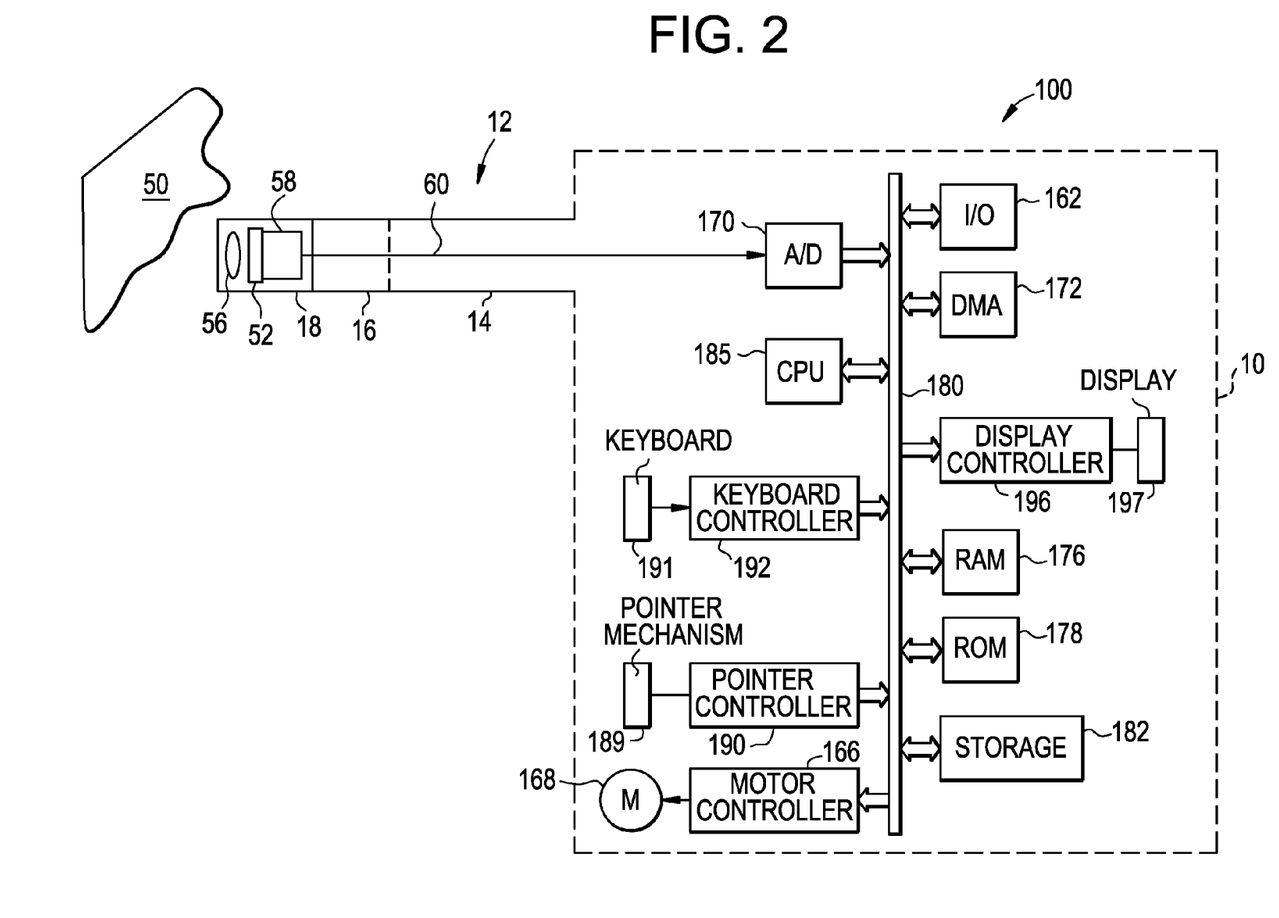
FIG. 2 is a schematic block electrical diagram of an exemplary inspection apparatus.

An exemplary block electrical diagram of an inspection apparatus is shown in FIG. 2. In the embodiment of FIG. 2, inspection apparatus 100 is shown as being provided by a visual inspection apparatus. However, as noted, inspection apparatus 100 can also be provided by e.g., an eddy current sensing apparatus or an ultrasonic sensing apparatus. An example of a commercially available visual inspection apparatuses is the XLG3 Video Borescope available from GE Inspection Technologies. An example of a commercially available eddy current sensing apparatus is the PHASEC 2d Eddy Current Flaw Detector available from GE Inspection Technologies. An example of a commercially available ultrasonic sensing apparatus is the PHASOR XS Portable Phased Array Ultrasonic Flaw Detector available from GE Inspection Technologies.

Referring to FIG. 2, incorporated in camera head assembly 18 can be image sensor 52 and lens 56 for focusing images of a target substrate 50 onto image sensor 52. Image sensor 52 can be a solid state two dimensional image sensor. Image sensor 52 can be provided in association with signal conditioning circuit 58 for use in inputting control signals to image sensor 52 and for use in conditioning image signals generated by image sensor 52.

Image signals generated by image sensor 52 are representative of light incident on the pixels of the image sensor 52. Image signals generated by image sensor 52 can be amplified by signal conditioning circuit 58 and can propagate through cable 60 for processing by circuitry of control and display module 10. Circuit components of a control and display module 10 in one embodiment are delimited by dashed in border of FIG. 2.

Image signals propagating on cable 60 can be received by analog to digital converter 170 and, after digitization by analog to digital converter 170 can be fed to random access memory 176 via system bus 180 so that the digitized image data can be accessed for processing by central processing unit (CPU) 185. A direct memory access device 172 (DMA) can be provided to facilitate the transfer of digitized image signals (image data) into RAM 176. Also included in a memory of apparatus 100 can be nonvolatile memory 178, e.g., an EPROM and a long term storage device 182, e.g., a hard drive. Also connected to system bus 180 can be various input devices such as pointer controller 190 and keyboard controller 192 and various output devices such as display controller 196. Further, keyboard controller 192 can also be in communication with keyboard 191, pointer controller 190 can be in communication with pointer mechanism 189, and display controller 196 can be in communication with display 197. Apparatus 100 can also include one or more communication interfaces 162. Interfaces 162 can be provided by an Ethernet network interface card (NIC) or wireless interface (e.g., an IEEE 802.11 compliant radio transceiver). There can also be coupled to system bus 180 a motor controller 166 for controlling motor 168 and for causing articulation of articulation cables 240, 242, 244, 246 of apparatus 100 to cause movement of an insertion tube 12.

CPU 185 can be programmed to carry out a variety of tasks, e.g., formatting of frames of image data for display of streaming video images on display 197 corresponding to light incident on image sensor 52, and formatting of frames of image data into formatized video formats for transmittal to external terminals. CPU 185 can also process control signals input by an operator using a control interface of apparatus 100 (which can comprise, e.g., a pointer mechanism 189 and keyboard 191) to output control signals to motor controller 166 for causing movement of articulation cables for causing movement of insertion tube 12.

Figure 3:
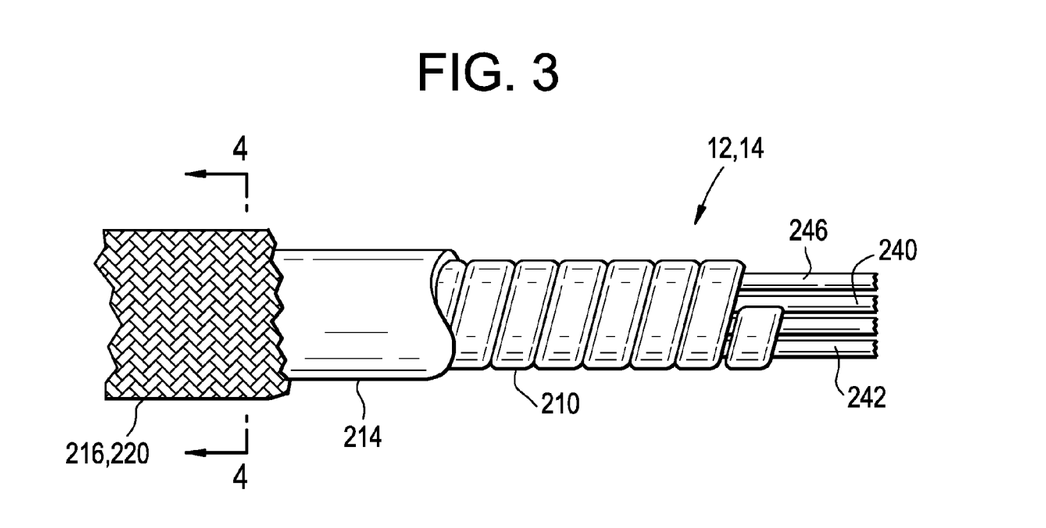
FIG. 3 is a cutaway side view of an insertion tube main body section.
Figure 4:
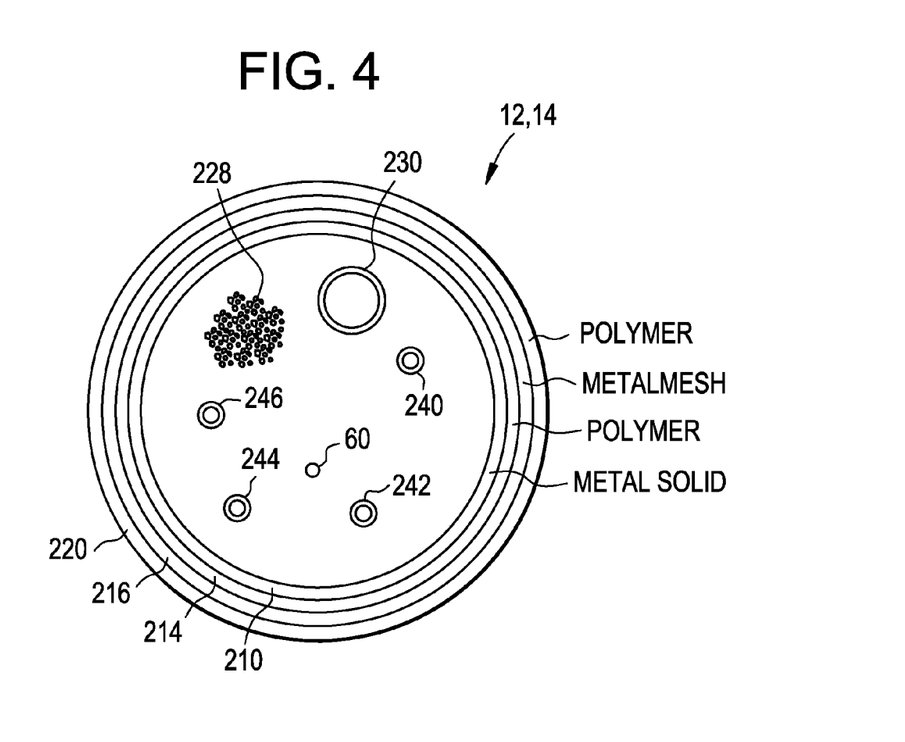
FIG. 4 is a cross sectional view of the insertion tube as shown in FIG. 3 taken along the line of 4-4 of FIG. 3.

Further aspects of insertion tube 12 in one embodiment are now described. As shown in FIGS. 3 and 4, the main body section of insertion tube 12 can be of a multilayer stacked up construction a cutaway side view of which is shown in FIG. 3, and a cross sectional view of which is shown in FIG. 4. As shown in FIG. 3, insertion tube 12 can comprise monocoil layer 210 typically comprising a metallic helical rigid coil as shown. Monocoil layer 210 provides crush resistance to insertion tube 12, protecting internal components of insertion tube 12, e.g., fiber optic bundles 228, working channels 230, and articulation cables 240, 242, 244, 246 from damage in case excessive forces are imparted from an external location to the insertion tube 12.

Figure 5:
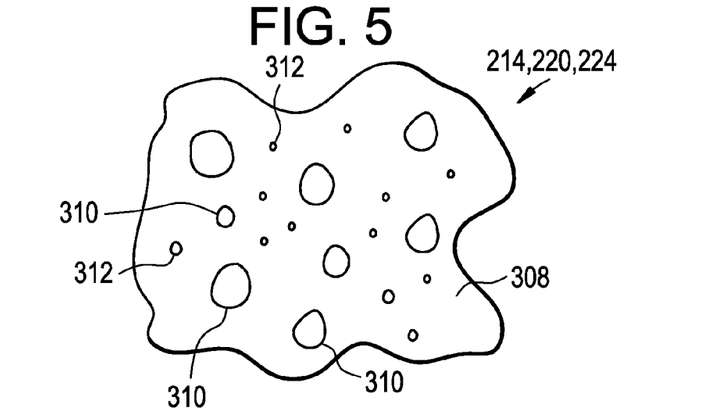
FIG. 5 is a schematic representation of an exemplary composite material having dispersed healing agent storage structures.

In one embodiment of apparatus 100, insertion tube 12 can be configured so that composite layer 214 adjacent to monocoil layer 210 is provided by a composite layer 214 having specifically formed healing agent storage structures and a catalyst dispersed in a polymer matrix. A representation of composite layer 214 is shown in FIG. 5. Composite layer 214 can have a polymer matrix 308 having dispersed therein healing agent storage structures 310 which can be adapted to store healing agent material. Further, composite layer 214 can have catalyst material 312 dispersed in polymer matrix 308 of the composite layer 214. Composite layer 214 can be configured so that when a force is imparted to composite layer 214, healing agent material stored in structure 310 reacts with the dispersed catalyst 312 of the polymer matrix to cause polymerization and repair of damage caused by impartation of the force. "Repair" herein shall refer to both complete repairs and partial repairs.

Referring to additional layers of an insertion tube main body section 14, which are represented in the cross sectional view of FIG. 4 as well as the cutaway side view of FIG. 3, insertion tube 12 can further include abrasion resistant layer 216 and associated coating layer 220. Abrasion resistant layer 216 can include wire mesh such as may be provided by tungsten mesh material. Coating layer 220 can be coated onto abrasion resistant layer 216 by way of dipping. In one embodiment, coating layer 220 can be provided by a traditional coating material such as urethane. In another embodiment, coating layer 220 like composite layer 214 can be provided by a composite having dispersed healing agent storage structures according to the description as provided in connection with layer 214; that is, a composite incorporating healing agent storage structures 310 and a catalyst 312 dispersed in a polymer matrix, the composite being configured so that when a force is imparted thereto healing agent material stored in a healing agent storage structure 310 can be released to react with the catalyst 312 to cause polymerization and repair of damage caused by the imparted force. Coating layer 220 like the composite layer 214 can take on the properties shown by FIG. 5, and therefore composite layer 214 as shown in FIG. 5 is further labeled with the reference numeral 220.

Figure 6:
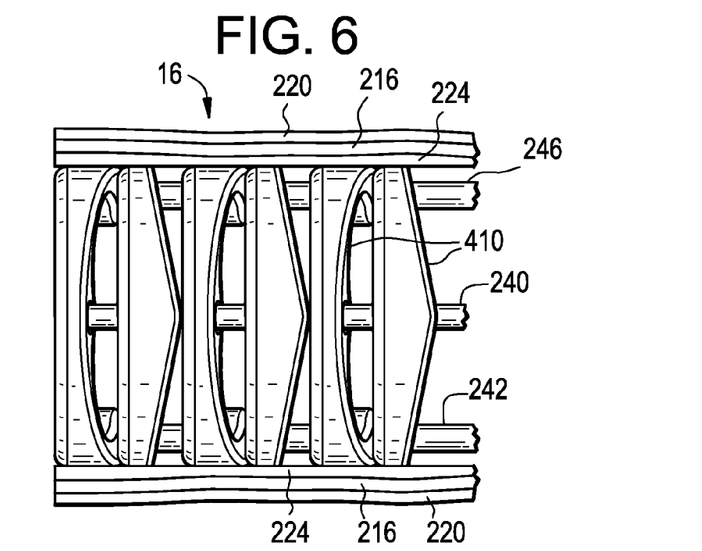
FIG. 6 is a cutaway side perspective view of an exemplary insertion tube bending neck.

Sections of the insertion tube 12 external to the main body section 14 can have construction different from the main body section 14. In FIG. 6 there is shown a bending neck section (bending neck 16) of an insertion tube 12 constructed in a manner described herein. Bending neck 16 can have a plurality of disks 410 aligned in series as shown. A pair of adjacent disks 410 can be moved between a first position in which the disks are aligned on a common axis and a second position where the disks are aligned on different axes defining an angle therebetween and wherein radial edges of the pair of disks are in contact with one another.

While the above arrangement provides for operator controlled bending of an insertion tube 12, the inventors also observed that the above arrangement leads to degradation and damage to an insertion tube 12 over time. Specifically, the inventors found that on repeated bendings of the bending neck 16, the rigid disks 410 impart forces on the walls of material surrounding the disks 410, degrading the material, and sometimes puncturing the material to allow entry of liquid and solid particulate into an interior of an insertion tube 12.

One embodiment described herein, a layer 224 adjacent to plurality of rigid disks 410 is formed of the composite material described herein; namely a composite material having a polymer matrix having dispersed therein storage structures storing healing agent material and also having dispersed therein a catalyst 312, the insertion tube 12 being arranged so that when a force is imparted to the composite material layer, a healing agent storage structure 310 can rupture to release healing agent material that reacts with the catalyst 312, to cause polymerization and repair of damage caused by the force impartation. As layer 224 can have characteristics previously described with reference to layer 214, the material composition design of FIG. 5 is further labeled with reference numeral 224. In such manner, as forces imparted by disks 410 to layer 224 degrade layer 224, layer 224 continually repairs itself through polymerization. As is indicated in the view of FIG. 6, bending neck 16 can have abrasion resistant layer 216 adjacent to layer 224 and coating layer 220 coated over abrasion resistant layer 216.

Figure 7:
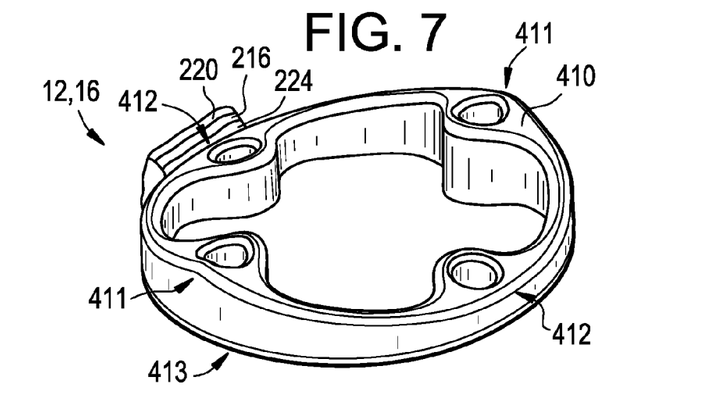
FIG. 7 is an internal perspective view of an insertion tube bending neck with a disk and a section of an insertion wall shown.
Figure 8:
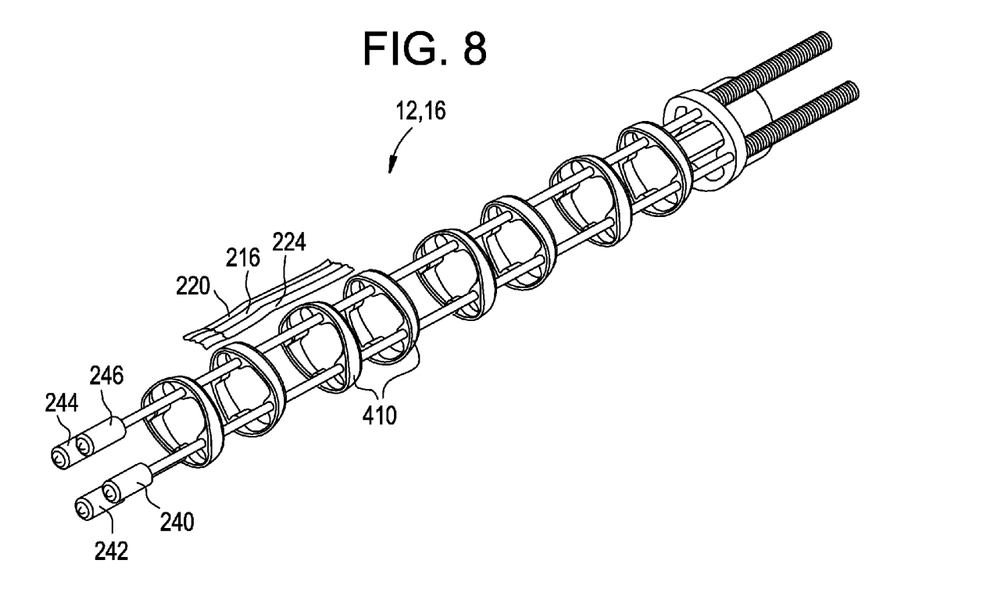
FIG. 8 is a perspective view of an insertion tube bending neck with a plurality of disks and a section of an insertion tube wall shown.
Figure 9:
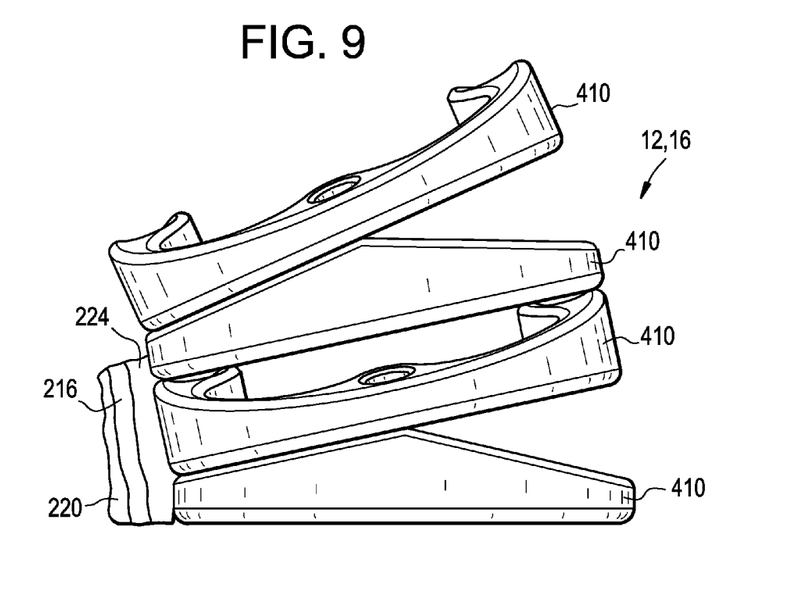
FIG. 9 is a cutaway side perspective view of an insertion tube bending neck showing a plurality of disks defining a row of disks in a curved orientation with a section of an insertion tube wall further shown.

Aspects of a bending neck 16, in one embodiment, are further described with reference to FIGS. 7, 8, and 9. Referring to FIG. 7, each disk 410 can have a configuration as shown in FIG. 7, with opposing peak edges 411 and valley edges 412 and a substantially flat back surface 413. A row of disks 410 can be arranged as shown in FIG. 8, with alternating disks 410 arranged 90 degrees apart so that a peak edge 411 of a first disk 410 touches a back surface of a second disk 410 at a location aligned with a valley of the second disk 410. The disks 410 can be arranged so that by appropriate forces imparted on a last disk 410 by cables 240, 242, 244, and 246, the orientation of a row of disks 410 changes. A row of disks 410 can be moved between a straight orientation as shown in FIG. 6, and a curved orientation as shown in FIG. 9.

More particular aspects of a healing agent storage structure 310 and polymer matrix composite layer, which may also be termed a self healing layer are described herein. Regarding a self healing layer, examples of suitable materials for use as a polymer matrix comprise EPON 828/DETA, or other epoxies, varnishes, polyurethanes, polycarbonates, and polyesters. Suitable structures for use as a healing agent storage structure 310 include hollow tubes and fibers, particles and microcapsules. In one embodiment where a healing agent storage structure 310 includes microcapsules, the microcapsules can be in the form of dicyclopentadiene (DCPD) monomer encapsulated in urea-formaldehyde shells. A suitable catalyst for initiating polymerization with DCPD microcapsules is bis(tricyclohexylphosphine) benzylideneruthenium (IV) dichloride, otherwise known as Grubbs' catalyst. Where the noted healing agent and catalysts are in contact, ring opening metathesis polymerization (ROMP) occurs to produce poly(dicyclopentadiene) (pDCPD). Aspects of various composite self-healing materials including healing agent storage structures dispersed in a polymer matrix for use in an insertion tube layer as described herein include S. White, N. Sottos, J. Moore. E. Brown, A. Jones, J. Rule, *Autonomic Healing of Polymers and Composites*, Theoretical and Applied Mechanics, University of Illinois Urbana-Champaign, Urbana, Ill. 61801, Aerospace Engineering, University of Illinois Urbana-Champaign, Urbana, Ill. 61801, Chemistry, University of Illinois Urbana-Champaign, Urbana, Ill. 61801, XXI International Congress of Theoretical and Applied Mechanics, Warsaw, Poland, Aug. 15-21, 2004, Ms. Jody W. C. Pang, Dr. Ian P. Bond, *A Hollow Fibre Reinforced Polymer Composite Encompassing Self-Healing and Enhanced Damage Visibility*, University of Bristol, Department of Aerospace Engineering, Queen's Building, University Walk, Bristol. BS8 1TR. UK. Tel: +44 (0) 117 928 8662 Fax: +44 (0) 117 927 2771 E-mail: I.P.Bond @Bristol.ac.uk, M. R. Kessler, N. R. Sottos, S. R. White, *Self-Healing Structural Composite Materials*, Department of Mechanical Engineering, University of Tulsa, 600 South College Avenue, Tulsa, Okla. 74104, USA, Department of Aerospace Engineering, University of Illinois at Urbana-Champaign, Urbana, Ill. 61801, USA, Department of Theoretical and Applied Mechanics, University of Illinois at Urbana-Champaign, Urbana, Ill. 61801, USA, Beckman Institute for Advanced Science and Technology, University of Illinois at Urbana-Champaign, Urbana, Ill. 61801, USA, received Jan. 24, 2003; revised Feb. 26, 2003; accepted Mar. 18, 2003.

A small sample of apparatuses that are described herein is as follows:

A1. An inspection apparatus comprising:
   a control and display unit comprising a display for display of data acquired by said inspection apparatus, and at least one control interface component for use in providing operator control of said inspection apparatus; and
   an elongated insertion tube having a proximal end and a distal end, said distal end for extending to a location in proximity with a target being subject to inspection, said elongated insertion tube being of multilayer stacked up construction having a plurality of layers, and wherein said layers of said multilayer elongated insertion tube include a monocoil layer for providing crush resistance to said elongated insertion tube, a metallic mesh layer, wherein said metallic mesh layer is disposed externally relative to said monocoil layer, a first composite layer and a second composite layer;
   wherein said first composite layer is disposed externally and adjacent to said monocoil layer and includes a polymer matrix and healing agent storage structures that store healing agent material dispersed in said polymer matrix, said first composite layer being adapted so that one of said storage structures of said first composite layer can rupture to release said healing agent material when a first force is imparted to said first composite layer, and wherein said healing agent material can react with a catalyst also dispersed in said polymer matrix of said first composite layer to initiate polymerization for healing of damage caused by said first force;
   wherein said second composite layer is disposed externally and adjacent to said metallic mesh layer and also includes a polymer matrix and healing agent storage structures that store healing agent material dispersed in said polymer matrix, said second composite layer defining an external surface of said inspection apparatus and being adapted so that one of said storage structures of said second composite layer can rupture to release said healing agent material of said second composite layer when a second force is imparted to said second composite layer, and wherein said healing agent of said second composite layer can react with a catalyst also dispersed in said polymer matrix of said second composite layer to initiate polymerization for healing of damage caused by said second force so that forces imparted by said monocoil layer can be received by said first composite layer and further so that forces imparted by a body external to said inspection apparatus can be received at said second composite layer.

A2. The inspection apparatus of A1, wherein said inspection apparatus is a video inspection apparatus having an image sensor disposed therein, and wherein said control and display module is adapted to display on said display streaming video images corresponding to light incident on said image sensor.

A3. The inspection apparatus of A1, wherein said inspection apparatus is an eddy current sensing apparatus.

A4. The inspection apparatus of A1, wherein said inspection apparatus is an ultrasonic sensing apparatus.

A5. The inspection apparatus of A1, wherein said insertion tube extends from said control and display unit.

A6. The inspection apparatus of A1, wherein said display and said at least one control interface component are supported on a common housing.

B1. An inspection apparatus comprising:
- a control and display unit comprising a display for display of data acquired by said inspection apparatus, and at least one control interface component for use in providing operator control of said inspection apparatus; and
- an elongated insertion tube having a proximal end and a distal end, said distal end for extending to a location in proximity with a target being subject to inspection, said insertion tube being of multilayer stacked up construction, and wherein said layers of said multilayer elongated insertion tube include a monocoil layer for providing crush resistance to said elongated insertion tube, and at least one composite layer;
- wherein said at least one composite layer is selected from the group consisting of
  - (a) a first composite layer disposed externally and adjacent to said monocoil layer and including a polymer matrix and healing agent storage structures that store healing agent material dispersed in said polymer matrix, said first composite layer being adapted so that one of said storage structures of said first composite layer can rupture to release said healing agent material when a force is imparted to said first composite layer, and wherein said healing agent material can react with a catalyst also dispersed in said polymer matrix of said first composite layer to initiate polymerization for healing of damage caused by said force; and
  - (b) a second composite layer disposed externally to said monocoil layer and defining an external surface of said insertion tube, said second composite layer including a polymer matrix and healing agent storage structures that store healing agent material dispersed in said polymer matrix, said second composite layer being adapted so that one of said storage structures of said second composite layer can rupture to release said healing agent material when a force is imparted to said second composite layer, and wherein said healing agent material can react with a catalyst also dispersed in said polymer matrix of said second composite layer to initiate polymerization for healing of damage caused by said force.

B2. The inspection apparatus of claim B1, wherein one of said layers includes a metallic mesh layer disposed externally to said monocoil layer, wherein said at least one composite layer comprises said second composite layer and wherein said second composite layer is disposed adjacent said metallic mesh layer.

B3. The inspection apparatus of claim B1, wherein said inspection apparatus includes said first composite layer.

B4. The inspection apparatus of claim B1, wherein said inspection apparatus includes said second composite layer.

B5. The inspection apparatus of claim B1, wherein said inspection apparatus includes said first composite layer and said second composite layer.

B6. The inspection apparatus of B1, wherein said inspection apparatus is a video inspection apparatus having an image sensor disposed therein, and wherein said control and display module is adapted to display on said display streaming video images corresponding to light incident on said image sensor.

B7. The inspection apparatus of B1, wherein said inspection apparatus is an eddy current sensing apparatus.

B8. The inspection apparatus of B1, wherein said inspection apparatus is an ultrasonic sensing apparatus.

B9. The inspection apparatus of B1, wherein said insertion tube extends from said control and display unit.

B10. The inspection apparatus of B1, wherein said display and said at least one control interface component are supported on a common housing.

C1. An inspection apparatus comprising:
- a control and display unit comprising a display for display of data acquired by said inspection apparatus, and at least one control interface component for use in providing operator control of said apparatus; and
- an elongated insertion tube having a proximal end and a distal end, said distal end for extending to a location in proximity with a target being subject to inspection, said insertion tube having disposed therein a plurality of articulation cable assemblies and including toward said distal end thereof a bending neck section, the bending neck section being characterized by a plurality of adjacently disposed disks, arranged in a row to define a row of disks wherein a pair of adjacent disks are capable of moving between axially aligned and axially misaligned relative orientations, and wherein said row of disks is capable of moving between straight and curved orientations, the bending neck section further being characterized by a composite layer disposed about said plurality of disks;
- wherein said composite layer includes a polymer matrix and healing agent storage structures that store healing agent material dispersed in said polymer matrix, said composite layer being adapted so that one of said storage structures of said composite layer can rupture to release said healing agent when a force is imparted to said composite layer, and wherein said healing agent can react with a catalyst also dispersed in said polymer matrix of said composite layer to initiate polymerization for healing of damage caused by said force.

C2. The inspection apparatus of C1, wherein said inspection apparatus further comprises a supplementary composite layer disposed external to said composite layer, said supplementary composite layer also including healing agent storage structures disposed in a polymer matrix.

C3. The inspection apparatus of C1, wherein said elongated insertion tube further comprises a metal mesh layer disposed external to said monocoil layer, and a supplementary composite layer disposed external to and adjacent relative to said metal mesh layer, said supplementary composite layer being formed by dipping said metal mesh layer.

D1. An insertion tube comprising:
- a proximal end and a distal end, said distal end for extending to a location in proximity with a target being subject to inspection, said insertion tube being of multilayer stacked up construction, and wherein said layers of said multilayer elongated insertion tube include a monocoil layer for providing crush resistance to said elongated insertion tube, and at least one composite layer;
- wherein said at least one composite layer is selected from the group consisting of
  - (a) a first composite layer disposed externally and adjacent to said monocoil layer and including a polymer matrix and healing agent storage structures that store healing agent material dispersed in said polymer matrix, said first composite layer being adapted so that one of said storage structures of said first composite layer can rupture to release said healing agent material when a force is imparted to said first composite layer, and wherein said healing agent material can react with a catalyst also dispersed in said polymer matrix of said first composite layer to initiate polymerization for healing of damage caused by said force; and (b) a second composite layer disposed externally to said monocoil layer and defining an external surface of said insertion tube, said second composite layer including a polymer matrix and healing agent storage structures that store healing agent material dispersed in said polymer matrix, said second composite layer being adapted so that one of said storage structures of said second composite layer can rupture to release said healing agent material when a force is imparted to said second composite layer, and wherein said healing agent material can react with a catalyst also dispersed in said polymer matrix of said second composite layer to initiate polymerization for healing of damage caused by said force.

D2. The insertion tube of claim D1, wherein one of said layers includes a metallic mesh layer disposed externally to said monocoil layer, and wherein said at least one composite layer comprises said second composite layer and wherein said second composite layer is disposed adjacent said metallic mesh layer.

D3. The insertion tube of claim D1, wherein said insertion tube includes said first composite layer.

D4. The insertion tube of claim D1, wherein said insertion tube includes a second composite layer.

D5. The insertion tube of claim D1, wherein said insertion tube includes said first composite layer and said second composite layer.

E1. An insertion tube comprising:
a proximal end and a distal end, said distal end for extending to a location in proximity with a target being subject to inspection, said insertion tube having disposed therein a plurality of articulation cable assemblies and including toward said distal end thereof a bending neck section, the bending neck section being characterized by a plurality of adjacently disposed disks, arranged in a row to define a row of disks wherein a pair of adjacent disks are capable of moving between axially aligned and axially misaligned relative orientations, and wherein said row of disks is capable of moving between straight and curved orientations, the bending neck section further being characterized by a composite layer disposed about said plurality of disks;
wherein said composite layer includes a polymer matrix and healing agent storage structures that store healing agent material dispersed in said polymer matrix, said composite layer being adapted so that one of said storage structures of said composite layer can rupture to release said healing agent when a force is imparted to said composite layer, and wherein said healing agent can react with a catalyst also dispersed in said polymer matrix of said composite layer to initiate polymerization for healing of damage caused by said force.

E2. The insertion tube of claim E1, wherein said insertion tube further comprises a supplementary composite layer disposed external to said composite layer, said supplementary composite layer also including healing agent storage structures disposed in a polymer matrix.

E3. The insertion tube of claim E1, wherein said elongated insertion tube further comprises a metal mesh layer disposed external to said monocoil layer, and a supplementary composite layer disposed external to and adjacent relative to said metal mesh layer, said supplementary composite layer being formed by dipping said metal mesh layer.

F1. An inspection apparatus comprising:
a control and display unit comprising a display for display of data acquired by said inspection apparatus, and at least one control interface component for use in providing operator control of said apparatus; and
an elongated insertion tube having a proximal end and a distal end, said distal end for extending to a location in proximity with a target being subject to inspection, said insertion tube being of multilayer stacked up construction, and wherein said layers of said multilayer elongated insertion tube include a metal mesh layer for providing abrasion resistance to said elongated insertion tube, and a composite layer;
wherein said composite layer is disposed external and adjacent to said metal mesh layer and includes a polymer matrix and healing agent storage structures that store healing agent material dispersed in said polymer matrix, said composite layer defining an outer surface of said elongated insertion tube and being adapted so that one of said storage structures of said composite layer can rupture to release said healing agent material when a force is imparted to said composite layer, and wherein said healing agent material can react with a catalyst also dispersed in said polymer matrix of said composite layer to initiate polymerization for healing of damage caused by said force.

G1. An inspection apparatus comprising:
a control and display unit comprising a display for display of data acquired by said inspection apparatus, and at least one control interface component for use in providing operator control of said inspection apparatus; and
an elongated insertion tube having a proximal end and a distal end, said distal end for extending to a location in proximity with a target being subject to inspection, said insertion tube being of multilayer stacked up construction, and wherein said layers of said multilayer elongated insertion tube include a monocoil layer for providing crush resistance to said elongated insertion tube, and a composite layer;
wherein said composite layer is disposed externally and adjacent to said monocoil layer and includes a polymer matrix and healing agent storage structures that store healing agent material dispersed in said polymer matrix, said composite layer being adapted so that one of said storage structures of said composite layer can rupture to release said healing agent material when a force is imparted to said composite layer, and wherein said healing agent material can react with a catalyst also dispersed in said polymer matrix of said composite layer to initiate polymerization for healing of damage caused by said force.

G2. The inspection apparatus of G1, wherein said inspection apparatus further comprises supplementary composite layer disposed external to said first composite layer, said supplementary composite layer also including healing agent storage structures that store healing agent material disposed in a polymer matrix.

G3. The inspection apparatus of G1, wherein said elongated insertion tube further comprises a metal mesh layer disposed external to said monocoil layer, and a supplementary composite layer disposed external to and adjacent relative to said metal mesh layer, said supplementary composite layer being formed by dipping said metal mesh layer.

While the present invention has been described with reference to a number of specific embodiments, it will be understood that the true spirit and scope of the invention should be determined only with respect to claims that can be supported by the present specification. Further, while in numerous cases herein wherein systems and apparatuses and methods are described as having a certain number of elements it will be understood that such systems, apparatuses and methods can be practiced with fewer than the mentioned certain number of elements.

The invention claimed is:

1. An inspection apparatus comprising:
a control and display unit comprising a display for display of data acquired by said inspection apparatus, and at least one control interface component for use in providing operator control of said inspection apparatus; and
an elongated insertion tube having a proximal end and a distal end, said distal end for extending to a location in proximity with a target being subject to inspection, said elongated insertion tube being of multilayer stacked up construction having a plurality of layers, and wherein said layers of said multilayer elongated insertion tube include:
a monocoil layer for providing crush resistance to said elongated insertion tube;
a metallic mesh layer comprising a mesh made of metal, wherein said metallic mesh layer is disposed externally relative to said monocoil layer;
a first composite layer disposed externally and adjacent to said monocoil layer and including a polymer matrix and healing agent storage structures that store healing agent material dispersed in said polymer matrix, said first composite layer being adapted so that one of said storage structures of said first composite layer can rupture to release said healing agent material when a first force is imparted to said first composite layer, and wherein said healing agent material can react with a catalyst also dispersed in said polymer matrix of said first composite layer to initiate polymerization for healing of damage caused by said first force; and
a second composite layer disposed externally and adjacent to said metallic mesh layer and also including a polymer matrix and healing agent storage structures that store healing agent material dispersed in said polymer matrix, said second composite layer defining an external surface of said inspection apparatus and being adapted so that one of said storage structures of said second composite layer can rupture to release said healing agent material of said second composite layer when a second force is imparted to said second composite layer, and wherein said healing agent of said second composite layer can react with a catalyst also dispersed in said polymer matrix of said second composite layer to initiate polymerization for healing of damage caused by said second force so that forces imparted by said monocoil layer can be received by said first composite layer and further so that forces imparted by a body external to said inspection apparatus can be received at said second composite layer.

2. An inspection apparatus comprising:
a control and display unit comprising a display for display of data acquired by said inspection apparatus, and at least one control interface component for use in providing operator control of said inspection apparatus; and
an elongated insertion tube having a proximal end and a distal end, said distal end for extending to a location in proximity with a target being subject to inspection, said insertion tube being of multilayer stacked up construction, and wherein said layers of said multilayer elongated insertion tube include:
a monocoil layer for providing crash resistance to said elongated insertion tube;
a composite layer disposed externally to said monocoil layer and defining an external surface of said insertion tube, said composite layer including a polymer matrix and healing agent storage structures that store healing agent material dispersed in said polymer matrix, said composite layer being adapted so that one of said storage structures of said composite layer can rupture to release said healing agent material when a force is imparted to said composite layer, and wherein said healing agent material can react with a catalyst also dispersed in said polymer matrix of said composite layer to initiate polymerization for healing of damage caused by said force and further so that forces imparted by a body external to said insertion tube can be received at said composite layer; and
wherein one of said layers includes a metallic mesh layer comprising a mesh made of metal disposed externally to said monocoil layer and wherein said composite layer is disposed externally and adjacent to said metallic mesh layer.

3. The inspection apparatus of claim 2, wherein said inspection apparatus includes a second composite layer between, and adjacent to, the monocoil layer and the metallic mesh layer, said second composite layer including a polymer matrix and healing agent storage structures that store healing agent material dispersed in said polymer matrix, said second composite layer being adapted so that one of said storage structures of said second composite layer can rupture to release said healing, agent material when a force is imparted to said second composite layer, and wherein said healing agent material can react with a catalyst also dispersed in said polymer matrix of said second composite layer to initiate polymerization for healing of damage caused by said force.

4. The inspection apparatus of claim 2, wherein said inspection apparatus is a video inspection apparatus having, an image sensor disposed therein, and wherein said control and display module is adapted to display on said display streaming, video images corresponding to light incident on said image sensor.

5. The inspection apparatus of claim 2, wherein said inspection apparatus is an eddy current sensing apparatus.

6. The inspection apparatus of claim 2, wherein said inspection apparatus is an ultrasonic sensing apparatus.

7. The inspection apparatus of claim 2, wherein said insertion tube extends from said control and display unit.

8. The inspection apparatus of claim 2, wherein said display and said at least one control interface component are supported on a common housing.

9. An insertion tube comprising:
a proximal end and a distal end, said distal end for extending to a location in proximity with a target being subject to inspection, said insertion tube being of multilayer stacked up construction, and wherein said layers of said multilayer elongated insertion tube include;
a monocoil layer for providing crush resistance to said elongated insertion tube;
a composite layer disposed externally to said monocoil layer and defining an external surface of said insertion tube, said composite layer including a polymer matrix and healing agent storage structures that store healing agent material dispersed in said polymer matrix, said composite layer being adapted so that one of said storage structures of said composite layer can rupture to release said healing agent material when a force is imparted to said composite layer, and wherein said healing agent material can react with a catalyst also dispersed in said polymer matrix of said composite layer to initiate polymerization for healing of damage caused by said force and further so that forces imparted by to body external to said insertion tube can be received at said composite layer; and wherein one of said layers further comprises a metallic mesh layer comprising a mesh made of metal disposed externally to said monocoil layer, and wherein said composite layer is disposed externally and adjacent to said metallic mesh layer.

10. The insertion tube of claim 9, wherein said insertion tube includes a second composite layer between, and adjacent to, the monocoil layer and the metallic mesh layer, said second composite layer including a polymer matrix and healing agent storage structures that store healing agent material dispersed in said polymer matrix, said second composite layer being adapted so that one of said storage structures of said second composite layer can rupture to release said healing agent material when a force is imparted to said second composite layer, and wherein said healing agent material can react with a catalyst also dispersed in said polymer matrix of said second composite layer to initiate polymerization for healing of damage caused by said force.

* * * * *

UNITED STATES PATENT AND TRADEMARK OFFICE
CERTIFICATE OF CORRECTION

| | | |
|---|---|---|
| PATENT NO. | : 8,356,527 B2 | Page 1 of 1 |
| APPLICATION NO. | : 12/187418 | |
| DATED | : January 22, 2013 | |
| INVENTOR(S) | : Hudson | |

It is certified that error appears in the above-identified patent and that said Letters Patent is hereby corrected as shown below:

In the Claims

In Column 12, Line 1, in Claim 2, delete "crash" and insert -- crush --, therefor.

In Column 12, Line 37, in Claim 4, delete "having," and insert -- having --, therefor.

In Column 12, Line 40, in Claim 4, delete "streaming," and insert -- streaming --, therefor.

In Column 12, Line 56, in Claim 9, delete "include;" and insert -- include: --, therefor.

In Column 13, Line 5, in Claim 9, delete "to body" and insert -- a body --, therefor.

Signed and Sealed this
Twenty-third Day of April, 2013

Teresa Stanek Rea
*Acting Director of the United States Patent and Trademark Office*